US012797563B2

(12) United States Patent
Zambelli

(10) Patent No.: US 12,797,563 B2
(45) Date of Patent: Nov. 17, 2026

(54) PRESSURED METERED DOSE INHALERS COMPRISING A BUFFERED PHARMACEUTICAL FORMULATION

(71) Applicant: CHIESI FARMACEUTICI S.P.A, Parma (IT)

(72) Inventor: Enrico Zambelli, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 877 days.

(21) Appl. No.: 17/760,354

(22) PCT Filed: Jan. 26, 2021

(86) PCT No.: PCT/EP2021/051669
§ 371 (c)(1),
(2) Date: Aug. 8, 2022

(87) PCT Pub. No.: WO2021/151857
PCT Pub. Date: Aug. 5, 2021

(65) Prior Publication Data

US 2023/0347080 A1 Nov. 2, 2023

(30) Foreign Application Priority Data

Jan. 28, 2020 (EP) .................................... 20153973
Dec. 15, 2020 (EP) .................................... 20214091

(51) Int. Cl.

| | |
|---|---|
| ***A61M 15/00*** | (2006.01) |
| ***A61K 9/00*** | (2006.01) |
| ***A61K 31/167*** | (2006.01) |
| ***A61K 31/56*** | (2006.01) |
| ***A61K 31/573*** | (2006.01) |
| ***A61K 31/575*** | (2006.01) |
| ***A61K 47/02*** | (2006.01) |
| ***A61K 47/06*** | (2006.01) |
| ***A61K 47/10*** | (2017.01) |

(52) U.S. Cl.
CPC ........... *A61M 15/009* (2013.01); *A61K 9/008* (2013.01); *A61K 31/167* (2013.01); *A61K 31/573* (2013.01); *A61K 47/02* (2013.01); *A61K 47/06* (2013.01); *A61K 47/10* (2013.01)

(58) Field of Classification Search
CPC ........ A61M 15/009; A61M 2205/0238; A61M 15/00; A61K 9/008; A61K 31/167; A61K 31/573; A61K 47/06; A61K 31/56; C09D 127/18; A61P 11/00
See application file for complete search history.

(56) References Cited

U.S. PATENT DOCUMENTS

| | | | |
|---|---|---|---|
| 3,236,458 | A | 2/1966 | Ramis et al. |
| 3,361,306 | A | 1/1968 | Grim et al. |
| 3,980,074 | A | 9/1976 | Watt et al. |
| 3,994,421 | A | 11/1976 | Hansen |
| 5,115,803 | A | 5/1992 | Sioutas |
| 5,435,297 | A | 7/1995 | Klein |
| 5,676,930 | A | 10/1997 | Jager et al. |
| 5,682,875 | A | 11/1997 | Blower et al. |
| 5,899,201 | A | 5/1999 | Schultz et al. |
| 6,423,298 | B2 | 7/2002 | McNamara et al. |
| 6,475,467 | B1 | 11/2002 | Keller et al. |
| 6,585,958 | B1 | 7/2003 | Keller et al. |
| 6,716,414 | B2 | 4/2004 | Lewis et al. |
| 6,739,333 | B1 | 5/2004 | Hoelz et al. |
| 6,983,743 | B2 | 1/2006 | Hoelz et al. |
| 7,479,572 | B2 | 1/2009 | Tanoury et al. |
| 8,313,732 | B2 | 11/2012 | Davies et al. |
| 8,420,060 | B2 | 4/2013 | Brambilla |
| 9,358,224 | B2 | 6/2016 | Bonelli et al. |
| 9,402,825 | B2 | 8/2016 | Pasquali et al. |
| 9,554,992 | B2 | 1/2017 | Brambilla et al. |
| 9,808,422 | B2 | 11/2017 | Pasquali et al. |
| 10,098,837 | B2 | 10/2018 | Scuri et al. |
| 10,159,645 | B2 | 12/2018 | Bonelli et al. |
| 10,596,113 | B2 | 3/2020 | Bonelli et al. |
| 10,596,146 | B2 | 3/2020 | Soni et al. |
| 10,596,149 | B2 | 3/2020 | Bonelli et al. |
| 10,617,638 | B2 | 4/2020 | Bonelli et al. |
| 10,617,669 | B2 | 4/2020 | Bonelli et al. |
| 10,737,044 | B2 | 8/2020 | Brambilla et al. |
| 10,806,701 | B2 | 10/2020 | Bonelli et al. |
| 11,389,401 | B2 | 7/2022 | Bonelli et al. |

(Continued)

FOREIGN PATENT DOCUMENTS

| | | | |
|---|---|---|---|
| CA | 2338680 | C | 10/2008 |
| CN | 1634565 | A | 7/2005 |

(Continued)

OTHER PUBLICATIONS

Baron, C., "Is Now the Time to Shake Up the pMDI Environment," ONdrugDelivery, Issue No. 106, pp. 10-13, accessed at https://www.ondrugdelivery.com/is-now-the-time-to-shake-up-the-pmdi-environment/, Frederick Furness Publishing Ltd., United Kingdom (Apr. 2020).
Da Rocha, S.R.P., et al., Pressurized Metered-Dose Inhalers. In Hickey, A.J., et al. Pharmaceutical Inhalation Aerosol Technology, Third Edition. pp. 427-453, Taylor & Francis, United Kingdom (2019).
DF30 Technology Platform, Aptar Pharma, Version 1, accessed at https://www.aptar.com/wp-content/uploads/2020/07/pdfs_df30.pdf, 4 pages (Dec. 2016).

(Continued)

*Primary Examiner* — Mina Haghighatian
(74) *Attorney, Agent, or Firm* — Morgan, Lewis & Bockius LLP

(57) ABSTRACT

The present invention generally relates to an aerosol formulation comprising formoterol and beclomethasone dipropionate, said formulation being contained in a coated can, particularly useful for the use in a pressurised metered dose inhaler for the treatment of respiratory diseases.

26 Claims, No Drawings

(56) References Cited

U.S. PATENT DOCUMENTS

| | | | |
|---|---|---|---|
| 11,426,538 | B2 | 8/2022 | Copelli et al. |
| 2002/0025299 | A1 | 2/2002 | Lewis et al. |
| 2003/0015191 | A1 | 1/2003 | Armstrong et al. |
| 2003/0041859 | A1 | 3/2003 | Abrams et al. |
| 2003/0143163 | A1 | 7/2003 | Akehurst et al. |
| 2004/0050960 | A1 | 3/2004 | Godfrey et al. |
| 2004/0101483 | A1 | 5/2004 | Muller-Walz et al. |
| 2004/0126325 | A1 | 7/2004 | Lewis et al. |
| 2004/0139965 | A1 | 7/2004 | Greenleaf et al. |
| 2005/0095206 | A1 | 5/2005 | Vega et al. |
| 2005/0130947 | A1 | 6/2005 | Biggadike |
| 2005/0175549 | A1 | 8/2005 | Goede et al. |
| 2005/0268915 | A1 | 12/2005 | Wassenaar et al. |
| 2005/0274378 | A1 | 12/2005 | Bonney et al. |
| 2005/0287076 | A1 | 12/2005 | Looker et al. |
| 2006/0083693 | A1 | 4/2006 | Lewis et al. |
| 2006/0118107 | A1 | 6/2006 | King |
| 2006/0171899 | A1 | 8/2006 | Adjei et al. |
| 2006/0257324 | A1 | 11/2006 | Lewis et al. |
| 2006/0269484 | A1 | 11/2006 | Knopeck et al. |
| 2007/0086953 | A1 | 4/2007 | Meakin et al. |
| 2007/0196285 | A1 | 8/2007 | Maus et al. |
| 2007/0251950 | A1 | 11/2007 | Bacon |
| 2008/0166305 | A1 | 7/2008 | Singh et al. |
| 2008/0190418 | A1 | 8/2008 | Miller et al. |
| 2008/0274189 | A1 | 11/2008 | Collingwood et al. |
| 2009/0020114 | A1 | 1/2009 | Brambilla et al. |
| 2009/0209502 | A1 | 8/2009 | Haeberlin et al. |
| 2010/0218760 | A1 | 9/2010 | Anderson et al. |
| 2010/0300437 | A1 | 12/2010 | Sivigny et al. |
| 2011/0011394 | A1 | 1/2011 | Edwards et al. |
| 2011/0061646 | A1 | 3/2011 | Crosby |
| 2011/0081301 | A1 | 4/2011 | Brambilla |
| 2011/0132355 | A1 | 6/2011 | Gerhart et al. |
| 2011/0146677 | A1 | 6/2011 | Bonelli et al. |
| 2011/0150782 | A1 | 6/2011 | Bonelli et al. |
| 2011/0150783 | A1 | 6/2011 | Bonelli et al. |
| 2011/0150784 | A1 | 6/2011 | Bonelli et al. |
| 2011/0155129 | A1 | 6/2011 | Stedman et al. |
| 2012/0085345 | A1 | 4/2012 | Zeng et al. |
| 2012/0204871 | A1 | 8/2012 | Vega |
| 2013/0000636 | A1 | 1/2013 | Jacuk et al. |
| 2014/0060531 | A1 | 3/2014 | Brambilla et al. |
| 2014/0109900 | A1 | 4/2014 | Jinks |
| 2014/0190478 | A1 | 7/2014 | Liu |
| 2014/0305429 | A1 | 10/2014 | Lewis |
| 2014/0363383 | A1 | 12/2014 | Bonelli et al. |
| 2014/0363384 | A1 | 12/2014 | Bonelli et al. |
| 2015/0150787 | A1 | 6/2015 | Lechuga-Ballesteros et al. |
| 2015/0182450 | A1 | 7/2015 | Bonelli et al. |
| 2015/0182459 | A1* | 7/2015 | Bonelli .................. A61K 47/02 128/200.23 |
| 2015/0306026 | A1 | 10/2015 | Bonelli et al. |
| 2015/0328144 | A1 | 11/2015 | Bonelli et al. |
| 2016/0032058 | A1 | 2/2016 | Ye et al. |
| 2016/0303044 | A1 | 10/2016 | Bonelli et al. |
| 2016/0303045 | A1 | 10/2016 | Bonelli et al. |
| 2016/0324778 | A1 | 11/2016 | Knopeck et al. |
| 2017/0079949 | A1 | 3/2017 | Bonelli et al. |
| 2017/0095444 | A1 | 4/2017 | Bonelli et al. |
| 2018/0028439 | A1 | 2/2018 | Scuri et al. |
| 2018/0079587 | A1* | 3/2018 | Jacuk ..................... B65D 83/38 |
| 2019/0046433 | A1 | 2/2019 | Bonelli et al. |
| 2019/0125989 | A1 | 5/2019 | Bromley-Davenport et al. |
| 2019/0183784 | A1 | 6/2019 | Stein et al. |
| 2019/0247339 | A1* | 8/2019 | Corr ....................... A61K 9/008 |
| 2022/0395454 | A1 | 12/2022 | Zambelli et al. |
| 2023/0080276 | A1* | 3/2023 | Zambelli .................. A61K 9/08 128/200.23 |
| 2023/0277451 | A1 | 9/2023 | Zambelli et al. |
| 2023/0347080 | A1 | 11/2023 | Zambelli |
| 2025/0082588 | A1 | 3/2025 | Zambelli et al. |

FOREIGN PATENT DOCUMENTS

| | | | |
|---|---|---|---|
| CN | 1874756 | A | 12/2006 |
| CN | 1950075 | A | 4/2007 |
| CN | 101548943 | A | 10/2009 |
| CN | 103052378 | A | 4/2013 |
| CN | 108289842 | A | 7/2018 |
| CN | 108289843 | A | 7/2018 |
| CN | 109715148 | A | 5/2019 |
| EP | 0132352 | A2 | 1/1985 |
| EP | 0412648 | A2 | 2/1991 |
| EP | 0546009 | B1 | 3/1995 |
| EP | 0673240 | B1 | 3/1999 |
| EP | 0820323 | B1 | 9/2003 |
| EP | 1400239 | A1 | 3/2004 |
| EP | 1894568 | A1 | 3/2008 |
| EP | 1157689 | B1 | 1/2009 |
| EP | 2201934 | A1 | 6/2010 |
| EP | 2223682 | * | 1/2012 |
| EP | 2486914 | A2 | 8/2012 |
| EP | 2606891 | A1 | 6/2013 |
| EP | 2706987 | B1 | 4/2015 |
| GB | 1219090 | A | 1/1971 |
| GB | 2312379 | A | 10/1997 |
| GB | 2415388 | A | 12/2005 |
| GB | 2554091 | A | 3/2018 |
| JP | 2013-151503 | A | 8/2013 |
| JP | 2017-114566 | A | 6/2017 |
| JP | 2019-088776 | A | 6/2019 |
| RU | 106098 | U1 | 7/2011 |
| WO | WO 1994013262 | A1 | 6/1994 |
| WO | WO 1994013263 | A1 | 6/1994 |
| WO | WO 1994027663 | A1 | 12/1994 |
| WO | WO-9632345 | A1 | 10/1996 |
| WO | WO 2000006121 | A1 | 2/2000 |
| WO | WO 2000007567 | A1 | 2/2000 |
| WO | WO 2000050112 | A1 | 8/2000 |
| WO | WO 2000053187 | A1 | 9/2000 |
| WO | WO-0189480 | A1 | 11/2001 |
| WO | WO 02072448 | A1 | 9/2002 |
| WO | WO 2002072449 | A1 | 9/2002 |
| WO | WO 2002083079 | A2 | 10/2002 |
| WO | WO-03074024 | A1 | 9/2003 |
| WO | WO 2004054580 | A1 | 7/2004 |
| WO | WO-2004075896 | A1 | 9/2004 |
| WO | WO-2005023330 | A2 | 3/2005 |
| WO | WO 2005074900 | A2 | 8/2005 |
| WO | WO 2005112902 | A2 | 12/2005 |
| WO | WO 2006008213 | A1 | 1/2006 |
| WO | WO-2006089656 | A2 | 8/2006 |
| WO | WO 2006097445 | A1 | 9/2006 |
| WO | WO 2006105401 | A2 | 10/2006 |
| WO | WO 2007015665 | A1 | 2/2007 |
| WO | WO 2007071313 | A2 | 6/2007 |
| WO | WO 2007077328 | A1 | 7/2007 |
| WO | WO 2007121913 | A2 | 11/2007 |
| WO | WO 2008000482 | A1 | 1/2008 |
| WO | WO 2008017575 | A1 | 2/2008 |
| WO | WO 2008025787 | A2 | 3/2008 |
| WO | WO 2009051818 | A1 | 4/2009 |
| WO | WO-2010138862 | A2 | 12/2010 |
| WO | WO 2011076841 | A2 | 6/2011 |
| WO | WO 2011076842 | A2 | 6/2011 |
| WO | WO 2011076843 | A2 | 6/2011 |
| WO | WO 2011095762 | A1 | 8/2011 |
| WO | WO-2012016845 | A2 | 2/2012 |
| WO | WO 2012158166 | A1 | 11/2012 |
| WO | WO 2014033057 | A1 | 3/2014 |
| WO | WO 2014046993 | A1 | 3/2014 |
| WO | WO-2015101575 | A1 | 7/2015 |
| WO | WO-2015101576 | A1 | 7/2015 |
| WO | WO-2017093755 | A1 | 6/2017 |
| WO | WO-2017093758 | A1 | 6/2017 |
| WO | WO-2018033598 | A1 | 2/2018 |
| WO | WO-2018051130 | A1 | 3/2018 |
| WO | WO-2018051131 | A1 | 3/2018 |
| WO | WO-2018051133 | A1 | 3/2018 |
| WO | WO 2019142214 | A1 | 7/2019 |
| WO | WO-2019211578 | A1 | 11/2019 |

(56) References Cited

FOREIGN PATENT DOCUMENTS

WO WO-2019236559 A1 12/2019
WO WO-2019236649 A1 12/2019
WO WO 2021033081 A1 2/2021
WO WO-2021110239 A1 6/2021
WO WO 2021151857 A1 8/2021
WO WO 2021165348 A1 8/2021
WO WO 2022074183 A1 4/2022

OTHER PUBLICATIONS

International Search Report and Written Opinion for International Application No. PCT/EP2021/051669, European Patent Office, Netherlands, mailed on Apr. 8, 2021, 10 pages.
International Search Report and Written Opinion for International Application No. PCT/EP2021/053936, European Patent Office, Netherlands, mailed on May 11, 2021, 10 pages.
Kehoe, W., and Sule, A., "Cutting the Carbon Impact: Crating a More Sustainable pMDI Component Supply Chain," ONdrugDelivery, Issue No. 112, pp. 15-18, accessed at https://www.ondrugdelivery.com/magazines/drug-delivery-environmental-sustainability112/, Frederick Furness Publishing Ltd., United Kingdom (Oct. 2020).
Kupczyk, M., et al., "Beclomethasone dipropionate, formoterol fumarate and glycopyrronium bromide as a combination therapy for chronic obstructive pulmonary disease," Expert Review of Respiratory Medicine, 13:5-11, Taylor & Francis, United Kingdom (Jan. 2019).
Moon, C., et al., "Delivery Technologies for Orally Inhaled Products: an Update," AAPS PharmSciTech 20(3):117, Springer Science+Business Media, Germany (Feb. 2019).
Noakes, T., et al., "The Future of Propellants for pMDIs," Drug Delivery to the Lungs 27, accessed at https://aerosol-soc.com/wp-content/uploads/2016/10/01.Noakes.pdf (2016).
Popovych, O., "Correlation Between Apparent ph and Acid or Base Concentration in the ASTM Medium," Analytical Chemistry 36(4):878-882, American Chemical Society, United States (Apr. 1964).
English language translation of Search Report for Russian Patent Application No. 2021104054/04 dated May 5, 2021, 3 pages.
English language translation of Office Action for Chinese Patent Application No. 202110100918.3 dated Jul. 28, 2023, 13 pages.
Certification Center for Licensed Pharmacists of the China Food and Drug Administration, "Professional Knowledge of Chinese Materia Medica," pp. 276-289, Chinese Medicine Science and Technology Publishing House, China (Jul. 2016).
Yang, M., et al., "Pharmaceutics of Traditional Chinese Medicine," China Traditional Chinese Medicine Press, pp. 396-4000, China (Jan. 2013).
A Study to Assess the Safety, Tolerability and Efficacy of NVA237 Versus Placebo, ClinicalTrials.gov archive view of NCT1005901, Dec. 2, 2009.
Acetylcholine Chloride, http://www.sigmaaldrich.com/catalog/product/sigma/a6625?lang=en&region=GB (retrieved Feb. 23, 2017).
"Asthma: Lung and Airways Disorders," Merck Manual Home Edition, accessed online on May 5, 2010 at www.merck.com/mmhe/print/sec04/ch044/ch044a.html.
Atrovent® HFA (ipratropium bromide) Inhalation Aerosol, NDA 21-527 (FDA) Chemistry Review (year 2004).
Avdeef, A., "pH-Metric log P. Part 1. Difference Plots for Determining Ion-Pair Octanol-Water Partition Coefficients of Multiprotic Substances," *Quant. Struct.-Act. Relat.*, vol. 11, pp. 510-517 (1992).
Bean, H.S. et al., "Advances in Pharmaceutical Sciences," Academic Press, London and New York, vol. 2, 1967, pp. 38-41.
Bender, M.L., "Mechanisms of Catalysis of Nucleophilic Reactions of Carboxylic Derivatives" Department of Chemistry, Illinois Institute of Technology, Sep. 28, 1959.
Braga, D. et al., "Making Crystals from Crystals: a green route to crystal engineering and polymorphism," *Chem. Commun.*, pp. 3635-3645 (2005).
Capon, B. et al., "A Comparison of Neighbouring Group Participation by Phenolic and Alcoholic Hydroxy-Groups in Ester Hydrolysis," *Chemical Communications*, pp. 389-390 (1971).
Carey, F.A. et al., Advanced Organic Chemistry, Fourth Edition, Part A: Structure and Mechanisms, Chapter 8 Reactions of Carbonyl Compounds, pp. 474-479 (2000).
"Chronic Obstructive Pulmonary Disease," Merck Manual Home Edition, accessed on Mar. 21, 2010 at www.merck.com/mmhe/print/sec04/ch045a.html.
"Datasheet for the Decision of Mar. 5, 2015," T2474/11-3.3.07 (2015), 21 pages.
Emer, E. et al., "Direct Nucleophilic $S_N1$-Type Reactions of Alcohols," *Eur. J. Org. Chem*, pp. 647-666 (2011), DOI 10.1002/ejoc.201001474.
Experimental Report (2017).
Ferreira, E., "Hammett Correlations and Their Applications in Elucidating Reaction Mechanism" Stoltz Group Literature Seminar, Jul. 17, 2003.
Ganderton, D et al., "The formulation and evaluation of a CFC-free budesonide pressurised metered dose inhaler," *Respiratory Medicine*, Supplement D, pp. S4-S9 (2003).
García-Marcos, L. et al., "Inhaled corticosteroids plus long-acting $\beta_2$-agonists as a combined therapy in asthma," *Expert Opinion Pharmacother*., vol. 4(1), pp. 23-39 (2003).
"Glycopyrrolate," O'Neil, Maryadele J. The Merck Index: An Encyclopedia of Chemicals, Drugs, and Biologicals. Whitehouse Station, N.J.: Merck, 2006, 4504.
"Glycopyrronium Bromide" in Martindale: The Complete Drug Reference, vol. 33, 2002, p. 467.
"Guidance for Industry, Nasal Spray and Inhalation Solution, Suspension, and Spray Drug Products—Chemistry, Manufacturing, and Controls Documentation," U.S. Department of Health and Human Services Food and Drug Administration Center for Drug Evaluation and Research (CDER), Jul. 2002, 49 pages.
Herdan, J.M et al., "Grafting Antioxidants: VIII. Antioxidant activity and grating of some N-(aryl)-2,6-di-tert-butylquinoneimines," *Polymer Degradation and Stability*, vol. 50, pp. 59-63 (1995).
Holland, G.F et al., "Labilization of Ester Bonds in Aminocyclitol Derivatives. I. Derivatives of myo- and scyllo-Inositols and of Streptamine," myo- and scyllo-Inositol Derivatives, Contribution from the National Institute of Arthritis and Metabolic Diseases, National Institutes of Health, and the Naval Medical Research Institute, vol. 80, Nov. 29, 1958, pp. 6031-6035.
Hopkinson, A.C. et al., "Acid-catalysed Hydrolysis of Alkyl Benzoates" *J. Chem. Soc. B*, pp. 203-205 (1969).
Huchon, G. et al., "Lung function and asthma control with beclomethasone and formoterol in a single inhaler," *Respiratory Medicine*, vol. 103, pp. 41-49 (2009).
Ingallinera, T.S. et al., "Compatibility of Glycopyrrolate Injection with Commonly Used Infusion Solutions and Additives" *Am. J. Hosp. Pharm*., vol. 36, pp. 508-510 (1979), with appended correction, *Am. J. Hosp. Pharm*., vol. 36, p. 745 (1979).
Kazempour, Abdol Rassoul, "The Alkaline Hydrolysis of Esters in Aqueous-Organic Solvent Mixtures," Postgraduate School of Studies in Chemistry, Oct. 1978.
Malik, A.U. et al., "The Effect of Dominant Alloy Additions on the Corrosion Behavior of Some Conventional and High Alloy Stainless Steels in Seawater," *Corrosion Science*, vol. 37(10), pp. 1521-1535 (1995).
March, J., Advanced Organic Chemistry, Fourth Edition, Reactions, Mechanisms, and Structure, pp. 378-398 (1992).
Mo, H. et al., "Closed-Shell Ion Pairs: Cation and Aggregate Dynamics of Tetraalkylammonium Salts in an Ion-Pairing Solvent," *J. Am. Chem. Soc*., vol. 119, pp. 11666-11673 (1997).
Narayanan, R., "Interfacial Processes and Molecular Aggregation of Surfactants," Advances in Polymer Science, ISSN 0065-3195, pp. 60 and 68-70 (2008).
Papi, A. et al., "Beclomethasone/formoterol versus budesonide/formoterol combination therapy in asthma," Eur. Respir J., vol. 29, pp. 682-689 (2007).
Physical Property Data Sheet for Zephex 134a, retrieved from http://www.mexichemfluor.com/products/medical/zephex134a/ on Sep. 23, 2016.

(56) References Cited

OTHER PUBLICATIONS

Purewal, T.S. et al., "Metered Dose Inhaler Technology," Interpharm Press Inc. US, (1998), pp. 10-17.
Rangaiah, V. et al., "Effect of Polarity of the Solvent on the Acid Hydrolysis of Nitrophenyl Esters," *Indian J. Chem.*, vol. 5, pp. 483-485 (1967).
Reichardt, C., "Solvents and Solvent Effect in Organic Chemistry," Third, Updated and Enlarged Edition, Wiley VCH, pp. 93-145, 17-154, 218-237, 273-292, and 526-555 (2003).
Seddon K.R., "Pseudopolymorph: A Polemic," *Crystal Growth & Design*, vol. 4(6), p. 1087 (2004).
Singh, D. et al., "Tolerability of high cumulative doses of the HFA modulite beclomethasone dipropionate/formoterol combination inhaler in asthmatic patients," *Pulmonary Pharmacology & Therapeutics*, vol. 21, pp. 551-557 (2008).
Singh, D., et al., "Triple therapy in COPD: new evidence with the extrafine fixed combination of beclomethasone dipropionate, formoterol fumarate, and glycopyrronium bromide," *International Journal of COPD*, vol. 12, pp. 2917-2928 (2017).
Singh, D., et al., "Single inhaler triple therapy versus inhaled corticosteroid plus long-acting $ß_2$-agonist therapy for chronic obstructive pulmonary disease (TRIOLOGY): a double-blind, parallel group, randomised controlled trial," *Lancet*, vol. 388, pp. 963-973 (2016).
Singh, D.et al., "The bronchodilator effects of extrafine glycopyrronium added to combination treatment with beclomethasone dipropionate plus formoterol in COPD: A randomized crossover study (the TRIDENT study)," *Respiratory Medicine*, vol. 114, pp. 84-90 (2016).
Streitwieser, A. Jr., et al., Introduction to Organic Chemistry, Second Edition, Chapter 5, pp. 86-88 and Chapter 19, pp. 539-548 (1973).
Sykes, P., "A guidebook to mechanism in organic chemistry," Fellow of Christ's College, Cambridge, Longman Group Ltd., pp. 238-244 (1961).
Tzou, T.-Z. et al., "Drug Form Selection in Albuterol-Containing Metered-Dose Inhaler Formulations and Its Impact on Chemical and Physical Stability," *Journal of Pharmaceutical Sciences*, vol. 86(12), pp. 1352-1357 (1997).
Vestbo, J. et al., "Trinity Manuscript Supplement", *Lancet*, Nov. 8, 2016 (21 pages).
Vestbo, J. et al., "Single inhaler extrafine triple therapy versus long-acting muscarinic antagonist therapy for chronic obstructive pulmonary disease (TRINITY): a double-blind, parallel group, randomized controlled trial," *Lancet*, vol. 389, pp. 1919-1929 (2017).
Vippagunta, S.R. et al., "Crystalline Solids," *Advanced Drug Delivery Reviews*, vol. 48, pp. 3-26 (2001).
Williams, R.O. III et al., "Advanced Drug Formulation Design to Optimize Therapeutic Outcomes," Informa Healthcare, NY (2008), pp. 23-36.
Williams, R.O. III et al., "Moisture Uptake and Its Influence on Pressurized Metered-Dose Inhalers," *Pharmaceutical Development and Technology*, vol. 5(2), pp. 153-162 (2000).
Vehring, R. et al., "Cosuspensions of Microcrystals and Engineered Microparticles for Uniform and Efficient Delivery of Respiratory Therapeutics from Pressurized Metered Dose Inhalers," Langmuir, vol. 28(42), pp. 15015-15023 (2012).
Vollhardt, K.P.C. et al., Organic Chemistry Structure and Function, Fifth Edition, W.H. Freeman and Company, pp. 334-337 (2007).
Yates, K. et al., "Mechanisms of Ester Hydrolysis in Aqueous Sulfuric Acids," Journal of the American Chemical Society, vol. 89(11), pp. 2686-2692 (1967).
"Single Inhaler Triple Therapy for COPD," Drug and Therapeutics Bulletin, vol. 55, pp. 138-141 (2017).
Corr, S. "Development of HFA-152a as a sustainable pMDI propellant," *Drug Delivery to the Lungs*, vol. 30, pp. 259-262 (2019).

* cited by examiner

PRESSURED METERED DOSE INHALERS COMPRISING A BUFFERED PHARMACEUTICAL FORMULATION

CROSS-REFERENCE TO RELATED APPLICATIONS

This application is a U.S. National Phase of International Application No. PCT/EP2021/051669, filed on Jan. 26, 2021, which claims the benefit of European Patent Application No. 20153973.1, filed Jan. 28, 2020, and European Patent Application No. 20214091.9, filed Dec. 15, 2020.

FIELD OF THE INVENTION

The present invention generally relates to an aerosol formulation comprising at least a LABA a corticosteroid and a propellant, said formulation being contained in a coated can, particularly useful for the use in a pressurised metered dose inhaler for the respiratory field.

BACKGROUND OF THE INVENTION

Pressurized metered dose inhalers (pMDIs) are well known devices for administering pharmaceutical products to the respiratory tract by inhalation. A pMDI device typically presents a medical-containing canister (or a “can” as herein referred to), and an actuator housing having a mouthpiece. The can is usually crimped with a metered valve assembly. Depending on the active ingredients and on additional components such as excipients, acids and similar, a final pMDI formulation may be in the form of a solution or a suspension. Solution is generally intended as substantially lacking precipitates or particles, while suspension typically refers to formulation having some undissolved material or precipitates. pMDI devices may use a propellant to expel droplets containing the pharmaceutical products to the respiratory tract as an aerosol. For many years the preferred propellants used in this respect were chlorofluorocarbons derivatives, which are commonly called Freons or CFCs, such as $CCl_3F$ (Freon 11 or CFC-11), $CCl_2F_2$ (Freon 12 or CFC-12), and $CClF_2$-$CClF_2$ (Freon 114 or CFC-114). Due to international concern that fully and partially halogenated chlorofluorocarbons possess a critical value of Global Warming Potential (GWP) impacting the earth’s protective ozone layer, many countries entered into an agreement, the Montreal Protocol, stipulating that their manufacture and use should be severely restricted and eventually phased out completely. Consequently, hydro fluoroalkanes (HFAs), in particular 1,1,1,2-tetrafluoroethane (HFA 134a) and 1,1,1,2,3,3,3-heptafluoropropane (HFA 227a) have been identified and accepted as substitutes to the CFCs in the pharmaceutical sector. Since then, the hydro fluoroalkanes propellants HFA 134a and HFA 227a have been widely used in the respiratory field, particularly considering their efficacy and compatibility with many active ingredients such as corticosteroids, LABA or antimuscarinic drugs.

However, despite the efficacy of said HFA propellants and despite their wide application in many pharmaceutical drugs already on the market, the possibility to have an alternative class of propellant and alternative means for obtaining effective pMDI devices are always under consideration. As general reference in this sense, see e.g. “Pharmaceutical Inhalation Aerosol Technology”, Third Edition 2019, Anthony J. Hickey et Al. wherein at page 440, Table 18.3 several propellants potentially suitable for medical use have been compared in terms of Global Warning Potential.

This is related for instance to the optimization of the mechanical components of the pMDI device, such as the valves or the cans, or even the possibility to have propellant-free nebulization devices, spray drying systems, or devices characterized by a more environmental friendly impact.

An additional feature worth to be considered when discussing a pMDI device, is the apparent pH and the water content of the formulation nebulized by said device. As a general reference in this sense, see e.g. WO 01/89480 and WO 03/074024.

Fluorocarbon polymers are commonly used to coat the interior can surfaces of pMDIs to eliminate particle adhesion, or deposition on can walls, i.e. avoiding the sticking, for suspension formulations and to avoid the formation of sub-products.

EP0820323 describes a pMDI having part or all of its internal surfaces coated with one or more fluorocarbon polymers for dispensing an inhalation drug formulation comprising salmeterol, and a fluorocarbon propellant, optionally in combination with one or more other pharmacologically active agents, wherein the coating of the interior can surfaces significantly reduces or essentially eliminates the problem of adhesion or deposition of salmeterol.

WO 2015/101576 describes a pMDI device particularly suitable for the use with a formoterol, beclomethasone dipropionate and glycopyrronium bromide solution, contained in a FEP coated can. As therein disclosed, the formulation contained in a FEP coated can is endowed with an improved stability and reduced amount of degradation products, mainly with regards to the N-(3-bromo)-[2-hydroxy-5-[1-hydroxy-2-[1-(4-methoxyphenyl)propan-2-ylamino]ethyl]phenyl]formamide. This product (identified as DP3) is, in fact, a particular degradation product originated by the interaction of formoterol and bromine ions from glycopyrronium bromide when the two active ingredients are dissolved in a HFA ethanol system in the presence of an acid, particularly hydrochloric acid.

EP2706987 describes a formulation for use in a pMDI device comprising beclomethasone dipropionate and HFA152, particularly suitable for the treatment of respiratory diseases.

WO2018/051131 describes in Example 1, Table 4 a pharmaceutical formulation comprising beclomethasone dipropionate and formoterol fumarate dihydrate, a propellant comprising 1,1-difluoroethane (HFA 152a) and glycerol, endowed with a good chemical stability. The exemplified formulations of WO2018/051131 are, in fact, characterized by the absence of any acid, and by the presence of glycerol.

WO2018/051130 describes a pharmaceutical formulation comprising a drug component comprising at least one pharmaceutically acceptable salt of glycopyrrolate and a propellant component comprising HFA 152a, wherein said formulation exhibits satisfactory stability without the use of acid stabilizers.

US20160324778, describes medicinal composition for use in a pressurized medicinal composition comprising a propellant selected form HFO-1234yf (2,3,3,3-tetrafluoropropene) and HFO-1234ze (1,3,3,3-tetrafluoropropene) and one or more active ingredient such as formoterol and beclomethasone dipropionate, wherein the active ingredient is in the form of a suspension or a solution with the propellant.

Although the above mentioned prior art provides effective formulations and devices technical arrangements, there is still the need to find a proper pMDI device for use in the respiratory field for the treatment of e.g. asthma and/or COPD, which not only contemplates the reduction of the greenhouse warming potential (GWP), but that also conveniently provides a good stabilization system, particularly regarding the calibration and maintenance of the apparent pH of the formulation contained in said device. It is in fact noticed that the prior art is silent about a proper and practical way to buffer the apparent pH of a formulation suitable for a pMDI device, comprising at least a corticosteroid, a LABA and a propellant. The apparent pH is in fact a crucial parameter which can impact many aspects of a pMDI formulation, especially when in the form of a solution, such as for instance, stability of the LABA agent, shelf life, consistent delivery of medication in aerosol from the MDI, the reproducibility of the final formulation and the maintenance of optimal chemical conditions within the can.

We have unexpectedly found that it is possible to stabilize the apparent pH of a formulation suitable for pMDI device comprising at least a corticosteroid, a LABA and a proper HFA or HFO propellant, by means of an internally coated can.

We have surprisingly found that the use of an internally coated can avoids the presence of a buffering agent to maintain stable the apparent pH of a pMDI formulation. In fact, the internally coated can according to the invention is able to stabilize the apparent pH, even for a prolonged period, as demonstrated in the herein below experimental part. In this sense, the coated can of the invention is able to act as an apparent pH buffering system.

Advantageously, said coated can containing at least a corticosteroid, a LABA and the selected HFA or HFO propellant of the invention may be cramped with a proper valve system, and readily used in a pMDI device for the treatment of respiratory diseases, such as asthma and/or COPD, also guaranteeing a good stability of the chemical components over the time, excellent aerosolizing performance, along with a low GWP.

SUMMARY OF THE INVENTION

In one aspect, the present invention refers to a can for use in a pMDI device, said can containing a formulation comprising at least a corticosteroid, a LABA agent and a HFA or HFO propellant, being said can internally coated by a coating comprising at least a compound selected from: an epoxy-phenol resin, a perfluorinated polymer, a perfluoroalkoxyalkane polymer, a perfluoroalkoxyalkylene polymer, a perfluoroalkylene polymer, poly-tetrafluoroethylene polymer (Teflon), fluorinated-ethylene-propylene polymer (FEP), polyether sulfone polymer (PES), a fluorinated-ethylene-propylene polyether sulfone polymer (FEP-PES), a polyamide, polyimide, polyamideimide, polyphenylene sulfide, plasma, mixtures or combinations thereof.

In a further aspect, the present invention refers to the above indicated can, provided with a metering valve system having at least a gasket made of an elastomeric material comprising: low-density polyethylene, butyl rubber such as chlorobutyl or bromobutyl rubber, butadiene-acrylonitrile rubbers, neoprene, EPDM (a polymer of ethylenepropylene-diene monomer), TPE (thermoplastic elastomer), cycloolefin copolymer (COC) or mixture thereof.

In one additional aspect, the present invention refers to the above indicated coated can, wherein said formulation comprising at least a corticosteroid, a LABA agent and HFA propellant is a solution, preferably also comprising a mineral or organic acid and/or a co-solvent.

In a further aspect, the invention refers to a pMDI device for use in the respiratory filed, particularly for treatment of asthma and/or COPD, comprising the above indicated coated can.

DETAILED DESCRIPTION OF THE INVENTION

Unless otherwise defined, all technical and scientific terms used herein have the same meanings as commonly understood by the skilled in the art.

"The "molar ratio" between formoterol or a salt thereof or a solvate of said salt and the acid is calculated considering the number of moles of formoterol or a salt thereof or a solvate of said salt within the formulation and number of moles of the selected acid in the formulation.

Unless otherwise provided, the term "formoterol fumarate" or "FF" refers to (R,R)-(±)formoterol fumarate or dihydrate thereof.

Unless otherwise indicated the term "LABA" or "LABA agent" includes in its meaning a long acting beta 2 agonist, as known in the art.

The term "% w/w" means the weight percentage of the component in respect to the total weight of the formulation.

The term "% w/v" means the weight percentage of the component in respect to the total volume of the formulation.

A "stable" composition as defined herein means that the content of residual active ingredient is of at least about 90% w/w (which is the content percent by weight with respect to its initial content at time 0), preferably of at least about 95% w/w, and that the total content of degradation product is of not more than about 10% by weight with respect to initial content of the active ingredient at time 0, preferably of not more than about 5% by weight, at a given time point, as measured by HPLC/UV-VIS.

Regarding the term "apparent pH" as herein intended, it is noticed that the calculation of the pH is generally characteristic of aqueous liquid, e.g. where water is the dominant component. In relatively aprotic solvents such as the HFA system of the present invention, protons are non-hydrated and their activity coefficients can differ from those in aqueous solution. Although the Nerst equation (describing potential of electrochemical cell as a function of concentrations of ions taking part in the reaction) with respect to electromagnetic field (EMF) applies and the pH-meter glass electrode system will generate a variable milli-volt output according to proton concentration and vehicle polarity, the pH meter reading represents the "apparent pH" according to the present invention. In this direction, the apparent pH according to the invention can be measured by technologies known in the art, as e.g. indicated in "Correlation between Apparent pH and Acid or Base Concentration in ASTM Medium" Orest Popovych, Analytical Chemistry 1964, 36, 4, 878-882; Analytical Standard Test Method (ASTM) D6423-19 "Standard Test Method for Determination of pH of Denatured Fuel Ethanol and Ethanol Fuel Blends".

As above mentioned, the present invention unexpectedly shows that when a coated can, suitable for a pMDI device, is used to contain a proper formulation comprising at least a corticosteroid, a LABA agent and an HFA or HFO propellant, the apparent pH of such formulation can be conveniently buffered between about 2.5 and 5, preferably between about 3 and 4.5, depending e.g. on the components of the formulation and/or on their amounts, as herein below described. Having such a buffering system brings several advantages, such as the increase in the stability of the formulation over the time, particularly regarding the formoterol amount, good shelf life, the reproducibility of the final formulation, the maintenance of optimal chemical conditions within the can and consistent delivery of medication in aerosol from the MDI.

In particular, having a stable apparent pH by means of an internally coated can avoids the addition of an external traditional acid-base buffering system, that would lead to a more complex formulation. On the contrary, non-internally coated cans do not show the effect of keeping the apparent pH constant over time for a pMDI solution formulation, as demonstrated in the herein below comparative examples.

Thus, in one embodiment, the invention refers to a can for use in a pMDI device, containing a formulation as herein described and claimed, characterized by the fact that the apparent pH of said formulation is stabilized at a value between about 2.5 and 5, preferably between about 3 and 4.5. In other words, the invention also refers to the herein described and claimed coated can, suitable for buffering the apparent pH of a formulation comprising at least a corticosteroid, a LABA and an HFA or HFO propellant, between about 2.5 and 5, preferably between about 3 and 4.5.

The apparent pH of the pMDI formulation is influenced by the composition of the formulation, e.g. with reference to the concentration of the acid and the like, and the setting of a proper value may be achieved by selecting a proper amount and type of LABA and/or corticosteroid agent, or by adding additional components to the formulation, as herein below described.

As far as the can is concerned, a coated can known in the art may be suitably used in the present invention. Thus, the can may be made of a metal, e.g. aluminum, or metal alloys, stainless steel or anodized aluminum, fluorine passivated aluminum and the like. Alternatively, the can may be made of plastic or any other suitable material. Preferably the can is made of aluminum, optionally anodized, or stainless steel, properly coated. The coating is typically applied to the internal surface of the can, thus providing an internal layer acting as interface between the internal surface of the can, and the formulation therein contained. By that, the internal coating will prevent the adherence of a component of the formulation on the can surface, also setting a pH buffering system. Typically, the internal coating will form a coating layer characterized by having a thickness that meets the uniformity and homogeneity requirements, as tested using e.g. WACO enamel rater instrument as e.g. available on the market. The internal coating will cover at least 90% of the internal surface of the can, preferably at least 95%, even more preferably, at least 99%.

In this regards, a suitable coated can of the invention may have part or all of its internal surfaces coated with an inert organic or inorganic coating preferably comprising: an epoxy-phenol resin, a perfluorinated polymer, a perfluoroalkoxyalkane polymer, a perfluoroalkoxyalkylene polymer (PFA), a perfluoroalkylene polymer, poly-tetrafluoroethylene polymer (PTFE or Teflon), fluorinated-ethylene-propylene polymer (FEP), polyether sulfone polymer (PES), a fluorinated-ethylene-propylene polyether sulfone polymer (FEP-PES), a polyamide, polyimide, polyamideimide, polyphenylene sulfide, plasma, mixtures or combinations thereof.

By way of example, the term "FEP-coated" refers to a coating layer comprising FEP, and optionally additional components including additives, adhesives, aggregation agents such as PES, isobutylketone and the like.

The above listed polymers may be used in combination with additional components, or as part of a polymeric mixture, obtained e.g. by blending together two or more polymeric compounds. In this direction, the internal coating of the can according to the invention is intended to comprise also said mixtures or combinations. In one embodiment, the coated can of the invention is a FEP or a PTFE coated can, or more preferably a FEP-PES coated can. In the case of FEP-PES coated, the PES acts as an intermediate layer between the internal surface and the FEP polymer, thus assuring an even more uniform and homogenous coating. It has in fact to be noted that, when suitable, more than one coating may be applied to the internal surface of the can, thus forming a bilayer or a multilayer coating having improved homogeneity and stability.

In one embodiment of the invention, the can is an aluminum can, characterized by having an internal coating comprising a FEP-PES polymer. Suitable aluminum FEP coated cans for the invention are those e.g. commercially available and used in the field.

As demonstrated in the herein below experimental part, when a formulation in form of a solution comprising at least beclomethasone dipropionate (BDP), formoterol fumarate dihydrateand a HFA propellant selected from HFA134a and HFA152a is contained in a FEP coated can according to the invention, the apparent pH of said formulation is conveniently maintained at a selected value, even for prolonged period of time. On the contrary, when an uncoated aluminum can (anodized or not) is used as comparative experiment, the apparent pH of the same solution shows an unstable profile over the time, as indicated in the herein below tables 1 and 2 (comparative).

In one embodiment, the corticosteroid component of the formulation contained in the coated can according to the invention, is selected from the group consisting of: budesonide, beclomethasone (BDP), e.g. as the mono or the dipropionate ester, flunisolide, fluticasone, e.g. as the propionate or furoate ester, ciclesonide, mometasone, e.g. as the furoate ester, mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocoritisone, desoxycorticosterone, rofleponide, etiprednol dicloacetate, wherein, beclomethasone dipropionate (BDP) and budesonide are particularly preferred. In a still preferred embodiment, the corticosteroid component is beclomethasone dipropionate (BDP).

The propellant of the formulation contained in the coated can according to the invention is selected from hydrofluoroalkanes (HFA) and hydrofluoroolefins (HFOs).

In one preferred embodiment, the HFA propellant of the formulation contained in the coated can according to the invention is selected from the group consisting of: 1,1,1,2-tetrafluoroethane (HFA134a), 1,1,1,2,3,3,3-heptafluoropropane (HFA227a), 1,1-difluoroethane (HFA152a) and mixtures thereof.

In a further preferred embodiment, the HFA propellant is selected from HFA134a and HFA152a or a mixture thereof.

In one preferred embodiment, the HFA propellant is HFA134a.

In one equally preferred embodiment the HFA propellant is HFA152a.

In one embodiment, the HFO propellant of the formulation contained in the coated can according to the invention is selected from the group consisting of: 1,3,3,3-tetrafluoropropene (HFO-1234ze) and 2,3,3,3-tetrafluoropropene (HFO-1234yf). Preferably the HFO propellant is HFO-1234ze.

Preferably, when the propellant is HFA134a, the amount of the corticosteroid component according to the present invention is comprised between 0.1-0.5% w/w, more preferably between 0.1-0.3% w/w, even more preferably between 0.1-0.2% w/w.

According to another embodiment, when the propellant is HFA152a, the amount of the corticosteroid component according to the present invention is comprised between 0.1-0.7% w/w, more preferably between 0.1-0.5% w/w, even more preferably between 0.2-0.4% w/w.

As far as the LABA component of the formulation contained in the coated can according to the invention is concerned, this is preferably selected from the group consisting of: salbutamol, (R)-salbutamol (levalbuterol), fenoterol, formoterol fumarate, arformoterol, carmoterol (TA-2005), indacaterol, milveterol, bambuterol, clenbuterol, vilanterol, olodaterol, abediterol, terbultaline, salmeterol, diastereoisomeric mixtures, and a pharmaceutically acceptable salt thereof or hydrate thereof. In one embodiment, the LABA is formoterol fumarate, preferably formoterol fumarate dihydrate. Preferably, when the propellant is HFA134a, the amount of LABA according to the present invention is comprised between 0.005-0.020% w/w, more preferably between 0.010-0.020% w/w, even more preferably between 0.010-0.016% w/w. In another embodiment, when the propellant is HFA152a, the amount of LABA according to the present invention is comprised between 0.005-0.030% w/w, more preferably between 0.010-0.027% w/w, even more preferably between 0.012-0.022% w/w.

The formulation contained in a coated can according to the invention may be in the form of a suspension or a solution. In one embodiment, the selected corticosteroids and LABA components are preferably dissolved in the HFA or HFO propellant as above defined, thus providing a solution. Hence, in one particularly preferred embodiment, the invention refers to a FEP coated can for use in a pMDI device, said FEP coated can containing a solution comprising at least beclomethasone dipropionate, formoterol fumarate dihydrate, and HFA 134a and/or HFA 152a.

As above set forth, the formulation contained in a coated can according to the invention, may optionally further comprise additional components such as excipients, additives, solvents, co-solvents, acids, low volatility components or even active ingredients. The addition of said components may be suitably calibrated in order to module e.g. the chemical-physical properties of the formulation and/or to set a proper apparent pH which is desired to be kept constant, according to the present invention. In this respect, in one preferred embodiment, the invention refers to a coated can for use in a pMDI device as above described, said coated can containing a formulation comprising a corticosteroid, a LABA agent, an HFA or HFO propellant, and optionally a co-solvent and/or an acid and/or a low volatile component.

Preferably, said co-solvent is a polar compound able to increase the solubility of the components within the formulation. Examples of suitable co-solvents are aliphatic alcohols having from 1 to 4 carbon atoms, such as methanol, ethanol, propanol, isopropanol and the like, preferably ethanol, more preferably anhydrous ethanol.

When present, said co-solvent is used in an amount comprised between 5% w/w and 20% w/w, more preferably between 10% and 15%.

In one embodiment, the acid may be a mineral or organic acid, preferably selected from: hydrochloric, hydrobromic acid, nitric acid, fumaric acid, phosphoric acid and citric acid, being hydrochloric particularly preferred. According to a still preferred embodiment, the acid is hydrochloric acid, concentrated or diluted, preferably 1M. When the acid is HCl 1M and the propellant is HFA 134a, it is used in an amount comprised between 0.010-0.050% w/w, preferably between 0.012-0.025% w/w, even more preferably between 0.015-0.025% w/w.

According to another embodiment, when the acid is HCl 1M and the propellant is HFA 152a, it is used in an amount comprised between 0.014-0.070% w/w, preferably between 0.016-0.035% w/w, even more preferably between 0.020-0.035% w/w.

In general, the amount of the chosen acid is preferably selected in order to have a final apparent pH of the solution comprised between about 2.5 and 5, preferably between 3 and 4.5, as above set forth. According to the invention, by using a coated can, the selected apparent pH is maintained stable and substantially unvaried over the time, even when said pH is set by the presence of an acid, thus solving the problem of how to control and stabilize the apparent pH of a formulation suitable for pMDI application, comprising at least a corticosteroid, a LABA agent and a propellant, in the presence of an inorganic or organic acid.

In one embodiment of the invention, the molar ratio between the LABA and the acid, when present, is comprised between 0.50 to 1.50, preferably between 0.9 and 1.1. It is in fact noticed that in this range the stability of the final formulation is increased up to a particularly convenient degree.

When present, the low volatility component has a vapor pressure at 25° C. lower than 0.1 kPa, preferably lower than 0.05 kPa, preferably selected from the group consisting of: glycols, propylene glycol, polyethylene glycol, glycerol or esters thereof, ascorbyl palmitate, isopropyl myristate and the like, wherein isopropyl myristate and glycerol are particularly preferred.

According to one embodiment, the formulation of the present invention contains an amount of water preferably below 3000 ppm, more preferably below 2000 ppm, still more preferably below 1500 ppm on the total weight of the formulation.

It is worth to note that by the present invention, the problem of how to effectively buffer an apparent pH of a pMDI formulation for commercial purposes comprising a corticosteroid, a LABA agent and an HFA or HFO propellant is surprisingly solved in the absence of additional buffering ingredients or agents, which could nevertheless compromise the stability and/or the efficacy of the formulation contained in the can. Also from a manufacturing point of view, the present invention allows the preparation of a pMDI device ready for use, comprising a coated can as herein detailed, with a simple and consolidated manufacturing process. Even further, the use of a green propellant such as HFA 152a or HFO-1234ze allows the present invention not only to solve the above expressed problems, but also to address potential environmental concerns arising from a prolonged use of other fluorinated propellants.

As above indicated, the coated can for use according to the present invention may also be characterized by additional technical features, such as the metering valve system. It is in fact surprisingly found that the use of a dedicated metering valve further increases the apparent pH buffering action of the coated can according to the invention, being also beneficial in terms of residual formoterol, overall stability and efficacy of the formulation.

Generally, the can of a pMDI device is crimped with a metering valve for delivering a therapeutically effective dose of the active ingredients. The metering valve assembly comprises at least a gasket seal. Preferably, the valve comprises 2 or 3 gaskets made of the same or different material. In this respect, according to the present invention, the valve is provided with 2 or 3 gaskets, made of the same material or different. Thus, according to the present invention, at least one gasket is made of a proper elastomeric material comprising at least one of polymer selected from: low-density polyethylene, butyl such as chlorobutyl or bromobutyl, butadiene-acrylonitrile, neoprene, EPDM (a polymer of ethylenepropylenediene monomer), TPE (thermoplastic elastomer), cycloolefin copolymer (COC) or combination thereof.

Preferably the valve is provided with 3 gaskets, even more preferably all of them made of EPDM, and herein referred as B-valve.

In one equally preferred embodiment, the valve is provided with a gasket made of COC, along with two gaskets made of EPDM, and herein referred as A-valve.

In an additional preferred embodiment, the valve is provided with two gaskets, preferably both of them made of chlorobutyl polymer, and herein referred as V-valve.

In one additional preferred embodiment, the valve is provided with a gasket made of butyl rubber, along with two gaskets made of EPDM.

The metering valve according to the invention is typically capable of delivering a volume in the range from 25 to 150 μl, preferably in the range from 50 to 100 μl, and more preferably of 50 μl or 70 μl per actuation. Suitable valves for the present invention are available on the market, e.g. from manufactures well known in the field.

Even further, depending on the selected HFA propellant, we have found that the choice of the valve may conveniently improve the efficacy and reliability of the final pMDI device. For example, when the HFA152a propellant is used in a coated can according to the present invention, the A-valve or the V-valve provides for an improvement of the stability of the final formulation, over e.g. the B-valve. This improvement in the stability is further enhanced if the formulation is in the form of a solution, as indicated in the present experimental part. The B-valve, in fact, when used in combination with the HFA152 propellant, may lead to a leakage of said propellant, that may result in an undesired loss of product, and possibly compromise the efficacy of the pMDI device over the time. Surprisingly, when the A-valve or the V-valve is used in combination with the HFA152a propellant in a coated can according to the invention, not only the apparent pH buffer action is maximized, but also the leakage of the formulation is substantially avoided. This results in an effective and convenient system to be readily employed in a final pMDI device. Advantageously, when the HFA134a propellant is used in a coated can according to the present invention either the B-valve or the A-valve or the V-valve may be conveniently used. This versatility confers a broad use and possibilities of customization of the final pMDI device containing the can according to the invention, thus accomplishing a variety of needs and requirements of the patients and/or of the market.

According to a preferred embodiment, when the propellant is HFA152a, the valve is selected from A-valve and V-valve, being A-valve even more preferred.

In an alternative embodiment, when the propellant is HFA134a, the valve is selected from B-valve, A-valve and V-valve, being B-valve and A-valve more preferred.

Thus, in one preferred embodiment, the invention refers to a FEP coated can for use in a pMDI device, said FEP coated can containing a formulation comprising at least BDP, formoterol fumarate dihydrate, HCl and HFA152a propellant, said FEP coated can having a valve selected from A-valve or V-valve. According to this embodiment, the can optionally further comprises ethanol, preferably anhydrous.

In a still additional embodiment, the invention refers to a FEP coated can for use in a pMDI device, containing a formulation comprising at least BDP, formoterol fumarate dihydrate, HCl and HFA134a propellant, said FEP coated can having a valve selected from B-valve, A-valve and V-valve, preferably V-valve or A-valve. According to this embodiment, the can optionally further comprises ethanol, preferably anhydrous.

The coated can for use in a pMDI device according to the present invention may be filled with the selected formulation by means of common methodologies used in the field.

As a general example said methodology may comprise the steps of:

a) preparing a solution comprising: formoterol fumarate, BDP and ethanol;
b) filling a FEP coated can with said solution;
c) adding an amount of HCl resulting in a molar ratio between formoterol fumarate dihydrate and the acid comprised between 0.50 to 1.50;
d) adding 1,1-difluoroethane (HFA 152a) propellant;
e) crimping with an Aptar valve and gassing.

The pMDI comprising the coated can according to the invention may have the configuration and components of a commonly used pMDI device, such as those already on the market for well-known formulations for treating e.g. asthma and/or COPD.

Unless otherwise provided, it is intended that all the above embodiments may be combined together and are to be considered as part of the scope of the present invention.

The invention will be now described by the following not limiting examples.

EXPERIMENTAL PART

In the below Examples 1 and 2, the apparent pH is measured using a standard LiCl electrode commonly used to measure the pH in organic media. Being MDI pressurized product, in order to measure the apparent pH of the formulation the following procedure was applied:

1—Cool down the canister up to at least −50° C. (deeping the canister in a dry ice bath or in liquid nitrogen, to allow to reduce the internal pressure to the atmospheric one).
2—Open the canister by cutting the valve and let the propellant evaporate at room temperature.
3—The remaining ethanolic solution (containing the API) is poured in a glass vial and bring to 10 ml volume with ethanol anhydrous to have a sufficient volume to be measured via a standard LiCl electrode.
4—Measure the apparent pH of the reconstituted solution using an LiCl electrode.

Example 1

An aluminum FEP coated can according to the invention was filled with a solution comprising Formoterol Fumarate dihydrate (0.010% w/w), BDP (0.172% w/w), HCl 1M (0.024% w/w) and Ethanol (12% w/w), in the presence of HFA134a (solution 1).

Similarly, an aluminum FEP coated can according to the invention was filled with a solution comprising FF (0.011% w/w), BDP (0.18% w/w), HCl 1M (0.026% w/w) and Ethanol (12% w/w), in the presence of HFA152a (solution 2).

The aluminum FEP coated cans filled with the solutions 1 or 2 and provided with valves A, B or V were put in stability chambers at 25 C°, 60% R.H. (relative humidity).

The Apparent pH (App pH) and the residual percentage of formoterol fumarate dihydrate (FF % w/w), over the initial content (100% at T=0) of both the solutions 1 and 2 were measured at T=0, after 1, 3 and 6 months respectively.

Results are collected in Table 1 below.

TABLE 1

Apparent pH value (App pH) and FF % in FEP coated can at T = 0 and T = 1 month (1 M); T = 3 months (3 M) and 6 months (6 M), measured at 25° C./60% R.H.

| Propellant | Can | Valve | T = 0 (App pH) | T = 1 M (App pH) | T = 3 M FF % w/w (App pH) | T = 6 M FF % w/w (App pH) |
|---|---|---|---|---|---|---|
| 134a | FEP | B-valve | (4.4) | (4.4) | 96.4 (4.5) | 92.9 (4.4) |
| 134a | FEP | A-valve | (4.1) | (4.1) | 95.6 (4.2) | 94.2 (4.0) |
| 134a | FEP | V-valve | (4.3) | (4.3) | 95.0 (4.3) | 92.3 (4.2) |
| 152a | FEP | A-valve | (4.7) | (4.7) | 98.9 (4.4) | 98.8 (4.2) |
| 152a | FEP | V-valve | (4.2) | (4.2) | 96.3 (4.2) | 95.9 (4.1) |
| 152a | FEP | B-valve | (4.4) | (4.4) | 97.4 (4.4) | 94.6 (4.3) |

B-valve: a valve provided with 3 gaskets, all of them made of EPDM, as e.g. available by Bespak.
A-valve: a valve provided with a gasket made of COC, along with two gaskets made of EPDM, as e.g. available by Aptar.
V-valve: a valve provided with two gaskets, both of them made of chlorobutyl polymer, as e.g. available by Vari.

Example 2 (Comparative)

The same analysis of Example 1 has been ran using uncoated aluminum can.

The Apparent pH (App pH) of both the solutions 1 and 2 according to Example 1 were measured at T=0, after 1, 3 and 6 months respectively, using different valve.

Results are collected in Table 2.

TABLE 2 apparent pH value (App pH) in uncoated can at T = 0 and T = 1 month (1 M); T = 3 months (3 M) and 6 months (6 M), measured at 25° C./60% R.H..

| Propellant | Uncoated CAN | Valve | T = 0 (App pH) | T = 1 M (App pH) | T = 3 M (App pH) | T = 6 M (App pH) |
|---|---|---|---|---|---|---|
| 134a | Al | B-valve | (4.6) | (5.0) | (5.5) | (5.7) |
| 134a | Al | A-valve | (4.8) | (5.2) | (5.6) | (5.7) |
| 134a | Al | V-valve | (4.7) | (5.1) | (5.2) | (5.4) |
| 152a | Al | B-valve | (4.7) | (5.0) | (5.4) | (5.4) |
| 152a | Al | A-valve | (4.6) | (4.9) | (5.2) | (5.3) |
| 152a | Al | V-valve | (4.5) | (5.1) | (5.6) | (5.5) |

B-valve: a valve provided with 3 gaskets, all of them made of EPDM, as e.g. available by Bespak.
A-valve: a valve provided with a gasket made of COC, along with two gaskets made of EPDM, as e.g. available by Aptar.
V-valve: a valve provided with two gaskets, both of them made of chlorobutyl polymer, as e.g. available by Vari.

As evident from the above Tables 1 and 2 the use of a FEP coated can according to the invention provided with the indicated Valves, guarantees a convenient stabilization of the pH of the therein contained solution, even for prolonged period of time, e.g. even after 6 months, when compared to T=0.

On the contrary, by using an uncoated can (comparative), the pH substantially increases with respect to the measure at T=0, also leading to a potential decreasing of the FF % w/w, even after just one month of storage at 25° C., which can be assumed to be the room temperature.

The invention claimed is:

1. A can for use in a pMDI device, wherein the can contains a formulation comprising at least a corticosteroid, a long acting beta 2 agonist (LABA) agent, and propellant 1,1-difluoroethane (HFA152a), wherein the can is internally coated by a coating comprising at least a fluorinated-ethylene-propylene polymer (FEP), the LABA agent is formoterol fumarate or formoterol fumarate dihydrate, and the can contains a valve selected from the group consisting of (i) a valve with a gasket made of cycloolefin copolymer (COC), along with two gaskets made of a polymer of ethylenepropylenediene monomer (EPDM) and (ii) a valve with two gaskets that are each made of chlorobutyl polymer.

2. The can according to claim 1, wherein the corticosteroid is selected from the group consisting of: budesonide, beclomethasone dipropionate, flunisolide, fluticasone, ciclesonide, mometasone, mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocoritisone, desoxycorticosterone, rofleponide and etiprednol dicloacetate.

3. The can according to claim 2, wherein the corticosteroid is beclomethasone dipropionate or budesonide.

4. The can according to claim 1, wherein the LABA agent is formoterol fumarate.

5. The can according to claim 3, wherein the LABA agent is formoterol fumarate dihydrate.

6. The can according to claim 1, wherein the formulation further comprises a co-solvent that is an aliphatic alcohol having from 1 to 4 carbon atoms.

7. The can according to claim 6, wherein the aliphatic alcohol is ethanol.

8. The can according to claim 1, wherein the formulation further comprises a mineral or organic acid selected from the group consisting of: hydrochloric acid, hydrobromic acid, nitric acid, fumaric acid, phosphoric acid and citric acid.

9. The can according to claim 8, wherein the acid is hydrochloric acid.

10. The can according to claim 1, wherein the formulation further comprises a low volatility component selected from the group consisting of: glycols, glycerol or esters thereof, ascorbyl palmitate, and isopropyl myristate.

11. The can according to claim 1, wherein the formulation is in the form of a solution.

12. The can according to claim 1, wherein the can contains a formulation having an apparent pH buffered between 2.5 and 5.

13. The can according to claim 12, wherein the formulation has an apparent pH buffered between 3 and 4.5.

14. A pMDI device comprising the can according to claim 1.

15. A method of treating a respiratory disease selected from asthma, chronic obstructive pulmonary disease (COPD), and a combination thereof, in a subject in need thereof, comprising administering to the subject the formulation comprising a corticosteroid and LABA agent using the pMDI device of claim 14.

16. A can for use in a pMDI device, wherein the can contains a formulation comprising a corticosteroid that is beclomethasone dipropionate or budesonide, formoterol fumarate dihydrate, and 1,1-difluoroethane (HFA152a), wherein the can is internally coated by a coating comprising a fluorinated-ethylene-propylene (FEP) polymer, wherein the formulation further comprises ethanol and hydrochloric acid, and wherein the can contains a valve containing one gasket comprising COC and two gaskets comprising EPDM.

17. A can for use in a pMDI device, wherein the can contains a formulation comprising a corticosteroid that is beclomethasone dipropionate or budesonide, formoterol fumarate dihydrate, and 1,1-difluoroethane (HFA152a), wherein the can is internally coated by a coating comprising a fluorinated-ethylene-propylene (FEP) polymer, wherein the formulation further comprises ethanol and hydrochloric acid, and wherein the can contains a valve containing two gaskets comprising butyl polymer, wherein the butyl polymer is chlorobutyl polymer.

18. The can according to claim 5, wherein the corticosteroid is beclomethasone dipropionate.

19. The can according to claim 16, wherein the corticosteroid is beclomethasone dipropionate.

20. The can according to claim 17, wherein the corticosteroid is beclomethasone dipropionate.

21. The can according to claim 16, wherein the formulation has an apparent pH between 2.5 and 5.

22. The can according to claim 17, wherein the formulation has an apparent pH between 2.5 and 5.

23. The can according to claim 5, wherein the formulation has an apparent pH between 2.5 and 5.

24. The can according to claim 18, wherein the formulation has an apparent pH between 2.5 and 5.

25. The can according to claim 19, wherein the formulation has an apparent pH between 2.5 and 5.

26. The can according to claim 20, wherein the formulation has an apparent pH between 2.5 and 5.

* * * * *